United States Patent
Lutz

(10) Patent No.: US 9,273,272 B2
(45) Date of Patent: Mar. 1, 2016

(54) NATURAL ANTIMICROBIAL COMPOSITIONS

(75) Inventor: Patrick Jay Lutz, Nazareth, PA (US)

(73) Assignee: LINCOLN MANUFACTURING INC., Lincoln, RI (US)

( * ) Notice: Subject to any disclaimer, the term of this patent is extended or adjusted under 35 U.S.C. 154(b) by 496 days.

(21) Appl. No.: 13/463,739

(22) Filed: May 3, 2012

(65) Prior Publication Data

US 2012/0282207 A1 Nov. 8, 2012

Related U.S. Application Data

(60) Provisional application No. 61/482,353, filed on May 4, 2011.

(51) Int. Cl.

| | | |
|---|---|---|
| A61K 8/00 | (2006.01) | |
| C11D 3/48 | (2006.01) | |
| C11D 3/20 | (2006.01) | |
| C11D 3/43 | (2006.01) | |
| C11D 9/26 | (2006.01) | |
| D21H 17/06 | (2006.01) | |
| D21H 17/14 | (2006.01) | |
| D21H 21/36 | (2006.01) | |
| A61K 8/34 | (2006.01) | |
| A61K 8/36 | (2006.01) | |
| A61K 8/368 | (2006.01) | |
| A61Q 5/02 | (2006.01) | |
| A61Q 5/12 | (2006.01) | |
| A61Q 17/00 | (2006.01) | |
| A61Q 19/00 | (2006.01) | |
| A01N 37/02 | (2006.01) | |
| C10L 1/14 | (2006.01) | |
| C10L 1/18 | (2006.01) | |
| C10L 1/188 | (2006.01) | |
| C10L 10/00 | (2006.01) | |
| C10M 129/02 | (2006.01) | |
| D21H 19/14 | (2006.01) | |
| C09D 5/14 | (2006.01) | |
| C10L 1/182 | (2006.01) | |
| C10L 1/189 | (2006.01) | |

(52) U.S. Cl.
CPC ........ *C11D 3/48* (2013.01); *A01N 37/02* (2013.01); *A61K 8/34* (2013.01); *A61K 8/345* (2013.01); *A61K 8/361* (2013.01); *A61K 8/368* (2013.01); *A61Q 5/02* (2013.01); *A61Q 5/12* (2013.01); *A61Q 17/005* (2013.01); *A61Q 19/00* (2013.01); *C10L 1/14* (2013.01); *C10L 1/18* (2013.01); *C10L 1/188* (2013.01); *C10L 10/00* (2013.01); *C10M 129/02* (2013.01); *C11D 3/2034* (2013.01); *C11D 3/2044* (2013.01); *C11D 3/2065* (2013.01); *C11D 3/2079* (2013.01); *C11D 3/2089* (2013.01); *C11D 3/2093* (2013.01); *C11D 3/43* (2013.01); *C11D 9/267* (2013.01); *D21H 17/06* (2013.01); *D21H 17/14* (2013.01); *D21H 21/36* (2013.01); *C09D 5/14* (2013.01); *C10L 1/1802* (2013.01); *C10L 1/1826* (2013.01); *C10L 1/1881* (2013.01); *C10L 1/1895* (2013.01); *C10L 2230/083* (2013.01); *C10M 2207/022* (2013.01); *C10M 2207/122* (2013.01); *C10M 2207/124* (2013.01); *C10M 2207/125* (2013.01); *C10M 2207/141* (2013.01); *C10M 2207/144* (2013.01); *C10N 2230/16* (2013.01); *D21H 19/14* (2013.01); *Y10T 428/4935* (2015.04); *Y10T 442/2525* (2015.04)

(58) Field of Classification Search
CPC .. C11D 3/2034; C11D 3/2044; C11D 3/2065; C11D 3/2079; C11D 3/2089; C11D 3/2093; C11D 3/43; C11D 3/48; C11D 9/267; D21H 17/06; D21H 17/14; D21H 19/14; D21H 21/36; A61K 8/34; A61K 8/345; A61K 8/361; A61K 8/368; A61Q 5/02; A61Q 5/12; A61Q 17/005; A61Q 19/00
See application file for complete search history.

(56) References Cited

U.S. PATENT DOCUMENTS

| | | | |
|---|---|---|---|
| 8,211,850 B2 * | 7/2012 | Andjelic et al. | 510/505 |
| 2006/0093634 A1 | 5/2006 | Lutz et al. | |
| 2007/0238780 A1 | 10/2007 | Lutz | |
| 2009/0208437 A1 | 8/2009 | Woehrmann et al. | |
| 2010/0234460 A1 | 9/2010 | Foret et al. | |
| 2010/0317734 A1 | 12/2010 | Folan et al. | |
| 2012/0201902 A1 * | 8/2012 | Modak et al. | 424/618 |

OTHER PUBLICATIONS https://en.wikipedia.org/wiki/Potassium_sorbate.*

* cited by examiner

*Primary Examiner* — Suzanne Ziska
(74) *Attorney, Agent, or Firm* — Blank Rome LLP

(57) ABSTRACT

The present invention provides novel antimicrobial compositions. In one embodiment, the antimicrobial composition comprises an antimicrobial effective amount of a mixture comprising (a) two or more fatty acids, each of which is natural or naturally derived, and (b) at least one of (i) a natural or naturally derived product, (ii) an alcoholic solvent, or (iii) an organic acid or a salt thereof. The present invention also provides a product comprising a preservative effective amount of the aforementioned mixture.

4 Claims, No Drawings

NATURAL ANTIMICROBIAL COMPOSITIONS

The present application claims the benefit of U.S. Provisional Application No. 61/482,353, filed May 4, 2011, which is hereby incorporated by reference.

FIELD OF THE INVENTION

The present invention relates to antimicrobial mixtures, for instance, comprising (a) two or more fatty acids, each of which is natural or naturally derived, and (b) at least one of (i) a natural or naturally derived product, (ii) an alcoholic solvent, or (iii) an organic acid.

BACKGROUND

There are many drawbacks to currently available natural and naturally-derived antimicrobial formulations. They are expensive, and high concentrations of them (for instance, >2%) are often required to prevent microbial growth and preserve a product. Many have undesirable colors and odors, have poor stability (for example, in aqueous systems), and are not effective against a broad spectrum of microorganisms. Additionally, some such natural or naturally-derived antimicrobial mixtures cause thinning of formulations. Many are oils or extracts which limits their usage in various formulations.

There is a continuing need for low cost and safe natural preservative systems which are effective against a broad spectrum of microorganisms.

SUMMARY OF THE INVENTION

The antimicrobial compositions of the present invention are relatively cheap to make, easy to work with and incorporate into finished products, generally have no odor, and have reduced (compared to prior oil preservative systems) or no color.

One embodiment of the present invention is an antimicrobial composition comprising an antimicrobial effective amount (such as a preservative, bactericidal, and/or fungicidal effective amount) of a mixture comprising:
(a) (i) two or more fatty acids, each of which is natural or naturally derived, or
(ii) a fatty acid and anisic acid, each of which is natural or naturally derived; and
(b) at least one of
(i) a natural or naturally derived product,
(ii) an alcoholic solvent, or
(iii) an organic acid or a salt thereof.

Preferred mixtures of the present invention include, but are not limited to, those shown in the table below.

| Mixture No. | Component (a) | Component (b) |
|---|---|---|
| 1 | Caprylic acid and Lauric acid | 1,3-Propanediol and Potassium Sorbate |
| 2 | Caprylic acid and Lauric acid | 1,3-Propanediol |
| 3 | Caprylic acid and Lauric acid | Glycereth-2 cocoate and Lactic acid |
| 4 | Caprylic acid and Lauric acid | 1,3 Propanediol and Benzoic acid |
| 5 | Caprylic acid and Lauric acid | Glycereth-2 cocoate |

The present inventor has discovered that the combination of (a) lauric acid, (b) caprylic acid, and (c) glycereth-2 cocoate or 1,3-propanediol acts synergistically against bacteria and fungi, is readily soluble in aqueous systems, can readily solubilize waxy fatty acids, and forms a stable concentrate. The inventor has also discovered that caprylic acid solubilizes lauric acid to form a stable antimicrobial mixture. Lauric acid is generally not soluble in aqueous solutions.

Another embodiment is an antimicrobial composition comprising an antimicrobial effective amount of a mixture comprising:
(a) caprylic acid (preferably natural or naturally derived),
(b) at least one waxy fatty acid, each of which is natural or naturally derived, and
(c) at least one of
(i) a natural or naturally derived product,
(ii) an alcoholic solvent, or
(iii) an organic acid.

In one embodiment, this mixture is present at a concentration of from about 0.01 to about 2% by weight, based on 100% total weight of the composition.

Yet another embodiment is an antimicrobial composition consisting essentially of an antimicrobial effective amount of a mixture consisting essentially of two or more fatty acids, each of which is natural or naturally derived. Suitable natural or naturally derived fatty acids include, but are not limited to, caprylhydroxamic acid, lauric acid, caprylic acid, capric acid, palmitic acid, and any combination of any of the foregoing. A preferred mixture consists essentially of caprylic acid and lauric acid. In a more preferred embodiment, the mixture consists essentially of at least about 50% by weight of caprylic acid, based upon 100% total weight of the antimicrobial mixture.

Yet another embodiment is an antimicrobial composition comprising an antimicrobial effective amount of a mixture comprising:
(a) caprylic acid, which is natural or naturally derived,
(b) a natural or naturally derived product,
(c) an alcoholic solvent (for example, natural benzyl alcohol), and
(d) optionally, an organic acid or a salt thereof.

In one preferred embodiment, the mixture comprises caprylic acid, glycereth-2 cocoate, and ethylhexyl glycerin.

Yet another embodiment is an antimicrobial composition comprising an antimicrobial effective amount of a mixture comprising:
(a) 1,3-propanediol (natural or naturally-derived),
(b) an alcoholic solvent (e.g., ethylhexyl glycerin), and
(c) optionally, an organic acid or a salt thereof (e.g., sorbic acid or a salt thereof).

In one preferred embodiment, the mixture comprises 1,3-propanediol (natural or naturally-derived), ethylhexyl glycerin, and potassium sorbate.

Preferred mixtures of the invention include, but are not limited to, those shown in the table below.

| Mixture No. | Component (a) | Component (b) | Component (c) |
|---|---|---|---|
| 6 | 1,3-Propanediol (natural or naturally-derived) | Ethylhexyl glycerin | Potassium sorbate |
| 7 | 1,3-Propanediol (natural or naturally-derived) | Benzyl alcohol (preferably natural benzyl alcohol) | Benzoic acid |
| 8 | 1,3-Propanediol (natural or naturally-derived) | Ethylhexyl glycerin | Benzoic acid |

-continued

| Mixture No. | Component (a) | Component (b) | Component (c) |
| --- | --- | --- | --- |
| 9 | 1,3-Propanediol (natural or naturally-derived) | Benzyl alcohol (preferably natural benzyl alcohol) | Caprylhydroxamic acid |
| 10 | 1,3-Propanediol (natural or naturally-derived) | Benzyl alcohol (preferably natural benzyl alcohol) | — |

One more preferred mixture comprises about 83% by weight of 1,3-propanediol (natural or naturally-derived), about 10% ethylhexyl glycerin, and about 7% potassium sorbate.

Preferably the mixtures of the present invention include an antimicrobial (e.g., preservative, bactericidal, and/or fungicidal) synergistic effective amount of the aforementioned ingredients. The antimicrobial composition is preferably substantially free or completely free of parabens (such as methylparaben, ethylparaben, and propylparaben). According to one embodiment, the antimicrobial composition contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of parabens, formaldehyde donors, and/or isothiazolinones, based upon 100% total weight of antimicrobial composition. In another embodiment, the antimicrobial composition is substantially free or completely free of synthetic preservatives. According to one embodiment, the antimicrobial composition contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of synthetic preservatives, based upon 100% total weight of antimicrobial composition.

Preferred mixtures of the present invention include, but are not limited to, those shown in the table below.

| Mixture No. | Component (a) | Component (b) |
| --- | --- | --- |
| 1 | about 45% caprylic acid + about 20% lauric acid | about 25% 1,3-propanediol + about 10% potassium sorbate |
| 2 | about 50% caprylic acid + about 25% lauric acid | about 25% 1,3-propanediol |
| 3 | about 60% caprylic acid | about 30% glycereth-2 cocoate + about 10% ethylhexyl glycerin (EHG) |
| 4 | about 40% caprylic acid + about 20% lauric acid | about 25% glycereth-2 cocoate + about 20% lactic acid |
| 5 | about 70% caprylic acid | about 30% lauric acid |
| 6 | about 80% 1,3-propanediol | about 10% ethylhexyl glycerin + about 10% potassium sorbate |
| 7 | about 45% caprylic acid + about 20% lauric acid | about 25% 1,3-propanediol + about 10% benzoic acid |

The pH of the concentrates of the antimicrobial mixtures of the present invention preferably have a pH below about 9.

In one embodiment, the antimicrobial mixtures of the present invention are used at a concentration of from about 0.1% to about 2% by weight.

In one preferred embodiment, the antimicrobial mixture includes caprylic acid and a waxy fatty acid (for instance, lauric acid). The inventors have found that caprylic acid facilitates solubilization and stability of the waxy fatty acid thereby enhancing its antimicrobial efficacy.

The antimicrobial mixtures and compositions of the present invention may be free or substantially free of oils.

Another embodiment is a method of killing and/or inhibiting the growth of microorganisms on a substrate or in or on a product by applying an effective amount of the antimicrobial composition of the present invention to the substrate or the product.

Yet another embodiment is a product comprising an antimicrobial, preservative, bactericidal, and/or fungicidal effective amount of the antimicrobial composition of the present invention. The product may be a solid or liquid. The antimicrobial compositions of the present invention are particularly effective as preservatives for personal care products.

Yet another embodiment is a method of preserving a product (e.g., a personal care product) by incorporating a preservative effective amount of the antimicrobial composition of the present invention into the product.

Yet another embodiment is a product (such as a shampoo) comprising a preservative effective amount of the antimicrobial composition of the present invention. The product is generally substantially free or completely free of parabens (such as methylparaben, ethylparaben, and propylparaben). The product may be, for example, a household (e.g., personal care), industrial, or institutional product. Preferred personal care products include, but are not limited to, shampoos, lotions (e.g., body lotions), conditioners, and soaps. Suitable household products include, but are not limited to, fabric softeners, laundry detergents, and hard surface cleaners. According to one embodiment, the product contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of parabens, based upon 100% total weight of product. According to one embodiment, the product does not contain a preservative effective amount of a preservative other than components (a) and (b) above. According to another embodiment, the only preservatives in the product are components (a) and (b). According to yet another embodiment, the product is all natural. According to yet another embodiment, the product contains less than a smelling or coloring effective amount of the antimicrobial composition.

In one embodiment, the product (for example, a shampoo) has a pH below about 8.

The components of these antimicrobial mixtures are natural thickening agents. Accordingly, they can be incorporated into formulations in a thickening effective amount (for example, to thicken a shampoo or other personal care product).

DETAILED DESCRIPTION OF THE INVENTION

Definitions

The term "microorganisms" includes, but is not limited to, bacteria, fungi, yeasts, algae, insects, and pests.

The term "personal care products" refers to products intended for application to the human body, such as to skin, hair, and nails, including, but not limited to, shampoos, conditioners, creams, lotions (such as body lotions), cosmetics, and soaps.

Components for the Antimicrobial Mixture

The natural or naturally derived fatty acid may be a waxy fatty acid. Suitable natural or naturally derived fatty acids include, but are not limited to, lauric acid, caprylic acid, capric acid, palmitic acid, and any combination of any of the foregoing. In one preferred embodiment, the antimicrobial mixture contains caprylic acid and a waxy fatty acid (such as lauric acid).

Suitable natural or naturally derived products include, but are not limited to, 1,3-propanediol (natural or naturally-derived), glycereth-2 cocoate, benzyl alcohol (naturally derived), glycerin, and any combination of any of the foregoing. A preferred natural or naturally derived product is 1,3-propanediol (natural or naturally-derived).

Suitable alcoholic solvents include, but are not limited to, ethylhexyl glycerin, phenoxyethanol, caprylyl glycols, pentylene glycol, hexylene glycol, and any combination of any of the foregoing.

Suitable organic acids and their salts include, but are not limited to, sorbic acid or a salt thereof (for example, potassium sorbate), benzoic acid or a salt thereof (for example, sodium benzoate), citric acid or a salt thereof, and any combination of any of the foregoing. Suitable salts of organic acids (such as sorbic acid and benzoic acid) include, but are not limited to, alkali metal or alkali earth metal salts, such as potassium and sodium.

Examples of Preferred Mixtures

Preferred mixtures include, but are not limited to, those in the table below. Preferred concentrations and preferred weight ratios are also provided in the table.

| Mixture No. | Component (a) | Component (b) | Preferred Weight Ratio of component (a) to (b) |
|---|---|---|---|
| 1 | from about 30 to about 60% caprylic acid and from about 5 to about 35% lauric acid | from about 10 to about 40% 1,3-propanediol and from about 5% to about 10% potassium sorbate | about 0.02:2 to about 0.025:2 |
| 2 | from about 30 to about 65% caprylic acid and from about 10 to about 40% lauric acid | from about 10 to about 40% 1,3-propanediol | about 0.02:2 to about 0.025:2 |
| 3 | from about 45 to about 75% caprylic acid | from about 15 to about 45% glycereth-2 cocoate and from about 5 to about 25% ethylhexyl glycerin | about 0.02:2 to about 0.025:2 |
| 4 | from about 25 to about 55% caprylic acid and from about 5 to about 35% lauric acid | from about 10 to about 40% glycereth-2 cocoate and from about 5 to about 35% lactic acid | about 0.02:2 to about 0.025:2 |
| 5 | from about 55 to about 85% caprylic acid | from about 15 to about 45% lauric acid | about 0.02:2 to about 0.025:2 |
| 6 | from about 65 to about 95% 1,3-propanediol | from about 5 to about 25% ethylhexyl glycerin and from about 5 to about 25% potassium sorbate | about 0.02:2 to about 0.025:2 |

Antimicrobial Compositions

The antimicrobial compositions of the present invention are useful as antimicrobial, fungicidal, and bactericidal agents (such as against allergens, tree and plant fungi, and plant and tree bacteria) and as preservatives in the papermaking, textile, agricultural, and coating industries and in personal care, household, industrial, and institutional products. The antimicrobial composition may be incorporated into substrates susceptible to microbial growth to preserve them. For example, the preservative system may be incorporated into or be a personal care product, such as a shampoo, conditioner, cream, lotion (such as body lotion), cosmetic, or soap; a household product, such as a fabric softener, laundry detergent, or hard surface cleaner; or an industrial product, such as paint, coatings, wood, textile, adhesive, sealant, leather, rope, paper, pulp, paper board, SHEETROCK™, ceiling tiles, plastic, fuel, petroleum, oil, rubber working fluid, metal working fluid, starches (such as pet food starch), or mineral slurry, such as a slurry of clay, calcium carbonate, or titanium oxide ($TiO_2$).

Generally, the product contains an antimicrobial, preservative, bactericidal, and/or fungicidal effective amount of the antimicrobial composition. According to one embodiment, the product contains from about 0.01 to about 2.0% by weight of each component of the antimicrobial composition, based upon 100% total weight of product. According to another embodiment, the product includes from about 0.1 to about 1 or 2% by weight of the antimicrobial composition, based upon 100% weight of total product.

Preservative Systems

The mixture of components discussed above (hereinafter referred to as "the preservative system") are useful as antimicrobial, fungicidal, and bactericidal agents (such as against allergens, tree fungi, and tree bacteria) and as preservatives in the papermaking, textile, agricultural, and coating industries and in personal care, household, industrial, and institutional products. The preservative system may be incorporated into substrates susceptible to microbial growth to preserve them. For example, the preservative system may be incorporated into or be a personal care product, such as a shampoo, conditioner, cream, lotion (such as body lotion), cosmetic, or soap; a household product, such as a fabric softener, laundry detergent, or hard surface cleaner; or an industrial product, such as paint, coatings, wood, textile, adhesive, sealant, leather, rope, paper, pulp, paper board, SHEETROCK™, ceiling tiles, plastic, fuel, petroleum, oil, rubber working fluid, metal working fluid, starches (such as pet food starch), or mineral slurry, such as a slurry of clay, calcium carbonate, or titanium oxide ($TiO_2$).

Generally, the antimicrobial composition and preservative system of the present invention acts quickly (e.g., reduces the microorganism (e.g., bacteria and/or fungi) count by 95, 99, 99.9, or 99.99% typically within an hour) and maintains efficacy (e.g., maintains less than 10 cfu/g) over long periods of time (e.g., for at least 7, 10, 14, or 28 days). The term "preservative effective amount" refers to an amount of the preservative system which maintains the microorganism count below 1000, 100, or 10 cfu/g for at least 1, 4, 7, 10, 14, or 28 days.

The antimicrobial composition and preservative system may include a solvent, such as water and water miscible solvents, including, but not limited to, alcohols (e.g., methanol, ethanol, propanol, iso-propanol, and butanol), glycols (e.g. glycerin, diglycerin, butylene glycol, butoxydiglycol, propylene glycol, and dipropylene glycol), esters, ethers, polyethers, and any combination of any of the foregoing. For example, the solvent may comprise water and one or more glycol and/or one or more alcohol, such as glycerin, phenoxyethanol, benzyl alcohol, or ethanol. A specific solvent system comprises water and a glycol, such as glycerin. A second specific solvent system comprises water and an alcohol, such as ethanol.

Other adjuvants may be included in the antimicrobial composition and preservative system as known to one of ordinary skill in the art. Suitable adjuvants include, but are not limited to, preservatives; solubilizing agents; chelating agents, such as ethylenediaminetetraacetic acid (EDTA) and salts thereof and zeolites; surfactants, such as cationic, anionic, nonionic, and amphoteric surfactants; antioxidants, such as butylated hydroxyanisole (BHA) and butylhydroxytoluene (BHT); amine oxides; tertiary amines; zinc compounds; hydrotropes; fluoride compounds; magnesium salts; calcium salts; carboxylic acids; phosphates; phosphonates; formaldehyde donors; glycereth-7; myristyl myristate; glutaraldehydes;

biguanides; natural products, such as geranoil, usnic acid, and tea tree oils; and any combination of any of the foregoing. Suitable preservatives include, but are not limited to, quaternary ammonium chlorides; quaternary ammonium carbonates; benzalkonium chloride; iodine containing compounds, such as 3-iodo-2-propynyl butyl carbamate (IPBC); hydantoins, such as dimethylhydantoin and halogenated hydantoins; isothiazolinones; parabens, such as methylparaben, ethylparaben, and propylparaben; dehydroacetic acid and salts thereof; isocil; chloroxylenol; chlorhexidine; phenoxyethanol; benzyl alcohol; phenethyl alcohol; benzoic acid and salts thereof such as sodium benzoate; chlorobutanol; sorbic acid and salts thereof; triclosan; triclocarban; and any combination of any of the foregoing.

The antimicrobial composition and preservative system may be incorporated into an aqueous or oil based system or an emulsion. A suitable solvent for an oil based system is phenoxyethanol and/or benzyl alcohol.

In one embodiment, the antimicrobial composition is comprised of all natural products.

The antimicrobial composition can be a liquid or a solid.

When the synergistic mixture contains only two components (i.e., two of (a), (b), and (c)) from the list above, the weight ratio of the first component to the second component typically ranges from about 0.01:100 to about 100:0.01, preferably ranges from about 0.1:20 to about 20:0.1, and more preferably ranges from about 1:10 to about 10:1. When the synergistic mixture contains three components, the third component can be in any amount, but typically the weight ratio of the third component to either of the first two components is from about 0.01:100 to about 100:0.01.

To prepare a formulation containing the product of the present invention, a concentrate of the antimicrobial composition and preservative system is generally first prepared. The concentrate may include from about 0.01 to about 100% by weight of the antimicrobial composition and preferably contains from about 5 to about 80% by weight of the antimicrobial composition, based upon 100% total weight of concentrate. For a two-component antimicrobial composition, the concentrate broadly contains from about 0.01 to about 99.99% by weight of the first component (e.g., component (a)) and from about 99.99% to about 0.01% by weight of the second component (i.e., component (b)) (based upon 100% total weight of concentrate). Table A illustrates the components and the ranges of components present in a typical concentrate for the two-component antimicrobial mixtures (based upon 100% total weight of concentrate).

TABLE A

| Ranges | Component (a) | Component (b) |
|---|---|---|
| Broad | from about 0.01 to about 99.99% | from about 99.99 to about 0.01% |
| Preferred | from about 5 to about 95% | from about 95 to about 5% |

Table B illustrates the components and the ranges of components present in a typical concentrate for the three-component antimicrobial mixtures (based upon 100% total weight of concentrate).

TABLE B

| Ranges | Component (a) [1,3-propanediol] | Component (b) [alcoholic solvent] | Component (c) [organic acid or salt thereof] |
|---|---|---|---|
| Broad | from about 0.01 to about 70% | from about 0.01 to about 70% | from about 0.01 to about 70% |
| Preferred | from about 5 to about 50% | from about 5 to about 50% | from about 5 to about 50% |

Before use, the concentrate is diluted, preferably with the same solvent as was used in the concentrate, and/or incorporated into a product. Use dilutions of the composition typically comprise an antimicrobial, preservative, fungicidally, or bactericidally effective amount of the antimicrobial composition.

Generally, use dilutions contain from about 0.0001% or 0.01% to about 2% by weight of the concentrate. According to one preferred embodiment, use dilutions contain from about 0.1 to about 1% by weight of the concentrate. In more preferred embodiments, the use dilution contains 0.2, 0.25 or 0.30% by weight of the concentrate. The use dilution generally contains from about 0.01, to about 2.0% by weight of each antimicrobial ingredient, based upon 100% total weight of use dilution. According to a preferred embodiment, the antimicrobial composition contains from about 0.001 to about 10%, preferably from about 0.01 to about 1%, and more preferably from about 0.05 to about 0.5% by weight of each antimicrobial ingredient (e.g., caprylic acid and/or lauric acid). Table C illustrates the components and generally the ranges of components present in the use dilution (based upon 100% total weight of use dilution) made from a two-component antimicrobial mixture.

TABLE C

| Ranges | Component (a) | Component (b) |
|---|---|---|
| Broad | from about 0.001 to about 10% | from about 0.001 to about 10% |
| Preferred | from about 0.01 to about 5% | from about 0.01 to about 5% |
| More Preferred | from about 0.05 to about 2% | from about 0.05 to about 2% |

Table D illustrates the components and generally the ranges of components present in the use dilution (based upon 100% total weight of use dilution) made from a three-component antimicrobial mixture.

TABLE D

| Ranges | Component (a) [1,3-propanediol] | Component (b) [alcoholic solvent] | Component (c) [organic acid or salt thereof] |
|---|---|---|---|
| Broad | from about 0.001 to about 10% | from about 0.001 to about 10% | from about 0.001 to about 10% |
| Preferred | from about 0.01 to about 5% | from about 0.01 to about 5% | from about 0.01 to about 5% |
| More Preferred | from about 0.05 to about 2% | from about 0.05 to about 2% | from about 0.05 to about 2% |

In another embodiment, the use dilution includes from about 0.01 to about 1% by weight of component (a), and from about 0.01 to about 1% by weight of component (b). In yet another embodiment, the use dilution includes from about 0.05 to about 0.5% by weight of component (a), and from about 0.05 to about 0.5% by weight of component (b).

According to another embodiment, the aforementioned antimicrobial composition is incorporated into a product at a concentration of about 0.1 to about 1 or 2% by weight, based upon 100% total weight of product.

Another embodiment of the present invention is a method for inhibiting the growth of microorganisms, bacteria (e.g., *S. aureus* (ATCC #6538), *P. aeruginosa* (ATCC #9027), and *E. coli* (ATCC #8739)), and/or fungi (including plant and tree fungi) (e.g., *Candida albicans, Aspergillus niger* and *Phytophthora ramrum*) on a substrate by applying an antimicrobial, preservative, bactericidal, or fungicidal effective amount of the antimicrobial composition of the present invention to the substrate. The antimicrobial composition may be applied to the substrate by any method known in the art including, but not limited to, brushing, dipping, soaking, vacuum impregnation, and pressure treatment.

The antimicrobial composition of the present invention may be prepared by mixing the antimicrobial components, and optionally, solvents, and adjuvants. The mixture may be heated and/or stirred to expedite mixing.

EXAMPLES

Example 1

The solubility and stability of 20% and 25% lauric acid in glycereth 2-cocoate, 1,3-propanediol, caprylic acid, and certain mixtures of them was determined. The results are shown below.

| Solvent | Solubility of 20% Lauric Acid | Solubility of 25% Lauric Acid |
| --- | --- | --- |
| Glycereth 2- Cocoate | Not Soluble | Not Soluble |
| 1,3 Propanediol | Not Soluble | Not Soluble |
| Caprylic acid | Soluble/Stable | Soluble/Stable |
| Caprylic acid + Glycereth 2- Cocoate | Soluble/Stable | Soluble/Stable |
| Caprylic acid + 1,3 Propanediol | Soluble/Stable | Soluble/Stable |

Example 2

The following compounds and mixtures were added to a DEA/sulfate shampoo system to assess their ability to act as thickeners. The results are provided below.

| Compound or Mixture | Thicken DEA/Sulfate Shampoo Systems without salt |
| --- | --- |
| 5% Glycereth 2- Cocoate | No |
| 5% 1,3 Propanediol | No |
| 2% Lauric/Caprylic acid | Yes |
| 2% Lauric/Caprylic acid + Glycereth 2- Cocoate | Yes |
| 2% Lauric/Caprylic acid + 1,3 Propanediol | Yes |

All references, patent applications, and patents cited herein are hereby incorporated by reference.

The invention claimed is:

1. An antimicrobial composition comprising an antimicrobial effective amount of a mixture comprising:
   (a) 1,3-propanediol,
   (b) ethylhexyl glycerin, and
   (c) potassium sorbate.

2. The antimicrobial composition of claim 1, wherein the composition contains from about 5 to about 50% by weight of 1,3-propanediol.

3. The antimicrobial composition of claim 1, wherein the composition contains from about 0.5 to about 2% by weight of 1,3-propanediol.

4. The antimicrobial composition of claim 1, wherein the composition comprises from about 65 to about 95% by weight of 1,3-propanediol, from about 5 to about 25% by weight of ethylhexylglycerin, and from about 5 to about 25% by weight of potassium sorbate.

* * * * *